United States Patent
Elsässer et al.

(10) Patent No.: US 10,634,624 B2
(45) Date of Patent: Apr. 28, 2020

(54) METHOD AND DEVICE FOR DETERMINING AN IRRADIATION PLAN FOR A PARTICLE IRRADIATION SYSTEM

(71) Applicants: Thilo Elsässer, Buckenhof (DE); Alexander Gemmel, Erlangen (DE); Thomas Hansmann, Leiman-Gauangelloch (DE); Eike Rietzel, Weiterstadt (DE)

(72) Inventors: Thilo Elsässer, Buckenhof (DE); Alexander Gemmel, Erlangen (DE); Thomas Hansmann, Leiman-Gauangelloch (DE); Eike Rietzel, Weiterstadt (DE)

(73) Assignee: Siemens Aktiengesellschaft, München (DE)

( * ) Notice: Subject to any disclaimer, the term of this patent is extended or adjusted under 35 U.S.C. 154(b) by 955 days.

(21) Appl. No.: 14/401,069

(22) PCT Filed: Mar. 28, 2013

(86) PCT No.: PCT/EP2013/056644
§ 371 (c)(1),
(2) Date: Nov. 13, 2014

(87) PCT Pub. No.: WO2013/170996
PCT Pub. Date: Nov. 21, 2013

(65) Prior Publication Data
US 2015/0100250 A1 Apr. 9, 2015

(30) Foreign Application Priority Data
May 14, 2012 (DE) .................. 10 2012 208 027

(51) Int. Cl.
*G01N 23/00* (2006.01)
*A61N 5/10* (2006.01)
*G01T 1/02* (2006.01)

(52) U.S. Cl.
CPC ............ *G01N 23/00* (2013.01); *A61N 5/1031* (2013.01); *G01T 1/02* (2013.01); *A61N 2005/1087* (2013.01)

(58) Field of Classification Search
CPC ............... A61N 5/1048; A61N 5/1031; A61N 2005/1087; G06F 19/3481; Y10S 378/901; G01N 23/00; G01T 1/02
(Continued)

(56) References Cited

U.S. PATENT DOCUMENTS

| 7,943,913 B2 * | 5/2011 | Balakin | H01J 3/04 250/423 R |
| 2002/0128807 A1 * | 9/2002 | Sakamoto | A61N 5/103 703/5 |

(Continued)

FOREIGN PATENT DOCUMENTS

| EP | 2221088 A1 | 8/2010 |
| WO | WO2008003526 A2 | 1/2008 |
| WO | WO-2011064004 A1 * | 6/2011 ........... A61N 5/1043 |

OTHER PUBLICATIONS

German Office Action for German Application No. 10 2012 208 027.9, dated Mar. 27, 2013, with English Translation.
(Continued)

*Primary Examiner* — Kyle R Quigley
(74) *Attorney, Agent, or Firm* — Lempia Summerfield Katz LLC

(57) ABSTRACT

The device relates to a method and a device (10) for determining an irradiation plan for a particle irradiation unit (20). In the method, a target volume (6) within a test object (14; 18) is irradiated with a particle beam (16) using the
(Continued)

particle irradiation unit (20) according to the irradiation plan. The radiation plan is determined in order to apply the energy of the particle beam (16) according to a predetermined dose distribution in the target volume (6), the target volume (6) and the predetermined dose distribution being pre-set. When determining the irradiation plan, irradiation duration is also taken into account, the irradiation plan being determined such that the irradiation duration is as short as possible.

16 Claims, 4 Drawing Sheets

(58) Field of Classification Search
USPC ......... 702/31, 89, 127, 150, 189; 250/492.1; 703/5
See application file for complete search history.

(56) References Cited

U.S. PATENT DOCUMENTS

| | | | | |
|---|---|---|---|---|
| 2004/0165696 | A1* | 8/2004 | Lee | A61N 5/1031 378/65 |
| 2006/0274885 | A1* | 12/2006 | Wang | G06Q 50/22 378/65 |
| 2010/0074408 | A1* | 3/2010 | Bert | A61N 5/103 378/65 |
| 2011/0248188 | A1* | 10/2011 | Brusasco | A61N 5/1048 250/492.1 |
| 2011/0297850 | A1* | 12/2011 | Claereboudt | A61N 5/10 250/492.1 |
| 2012/0238795 | A1* | 9/2012 | Bert | A61N 5/1043 600/1 |

OTHER PUBLICATIONS

Inaniwa T. et al., "Optimization for fast-scanning irradiation in particle therapy," Medical Physics, vol. 34 (8), pp. 3302-3311, 2007.

M. Krämer, O. Jäkel, T. Haberer et al. "Treatment planning for heavy-ion radiotherapy: physical beam model and dose optimization," Phys. Med. Biol. 45, p. 3299-3317, 2000.

Pardo J. et al. "Heuristic optimization of the scanning path of particle therapy beams," Medical Physics, vol. 36, No. 6, pp. 2043-2051, Jun. 1, 2009.

PCT International Search Report and Written Opinion of the International Searching Authority dated Jul. 31, 2013 for corresponding PCT/EP2013/056644.

Zenklusen S. M. et al. "A study on repainting strategies for treating moderately moving targets with proton pencil beam scanning at the new Gantry 2 at PSI," Physics in Medicine and Biology. vol. 55, pp. 5103-5121, CH, Aug. 11, 2010.

* cited by examiner

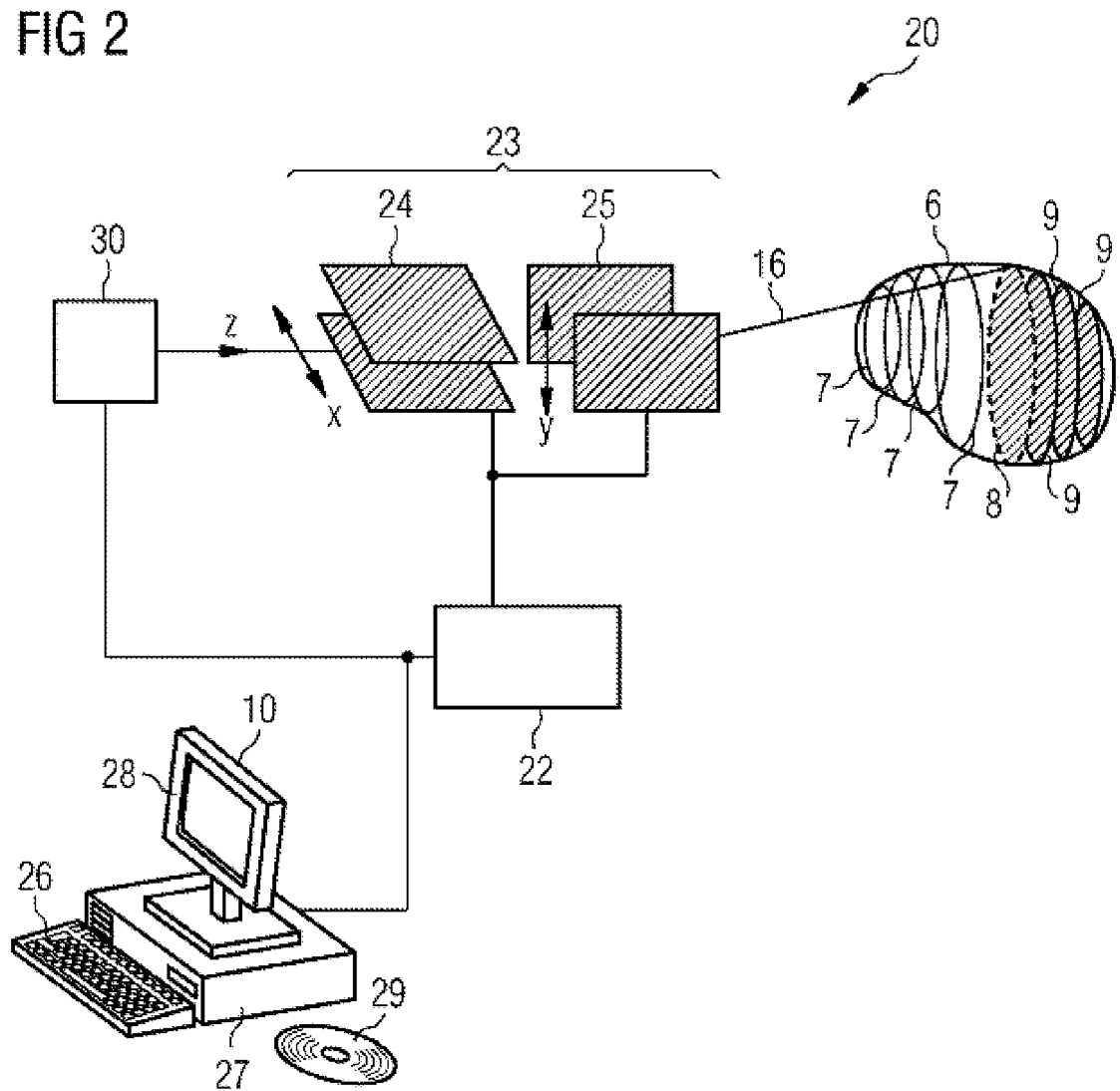

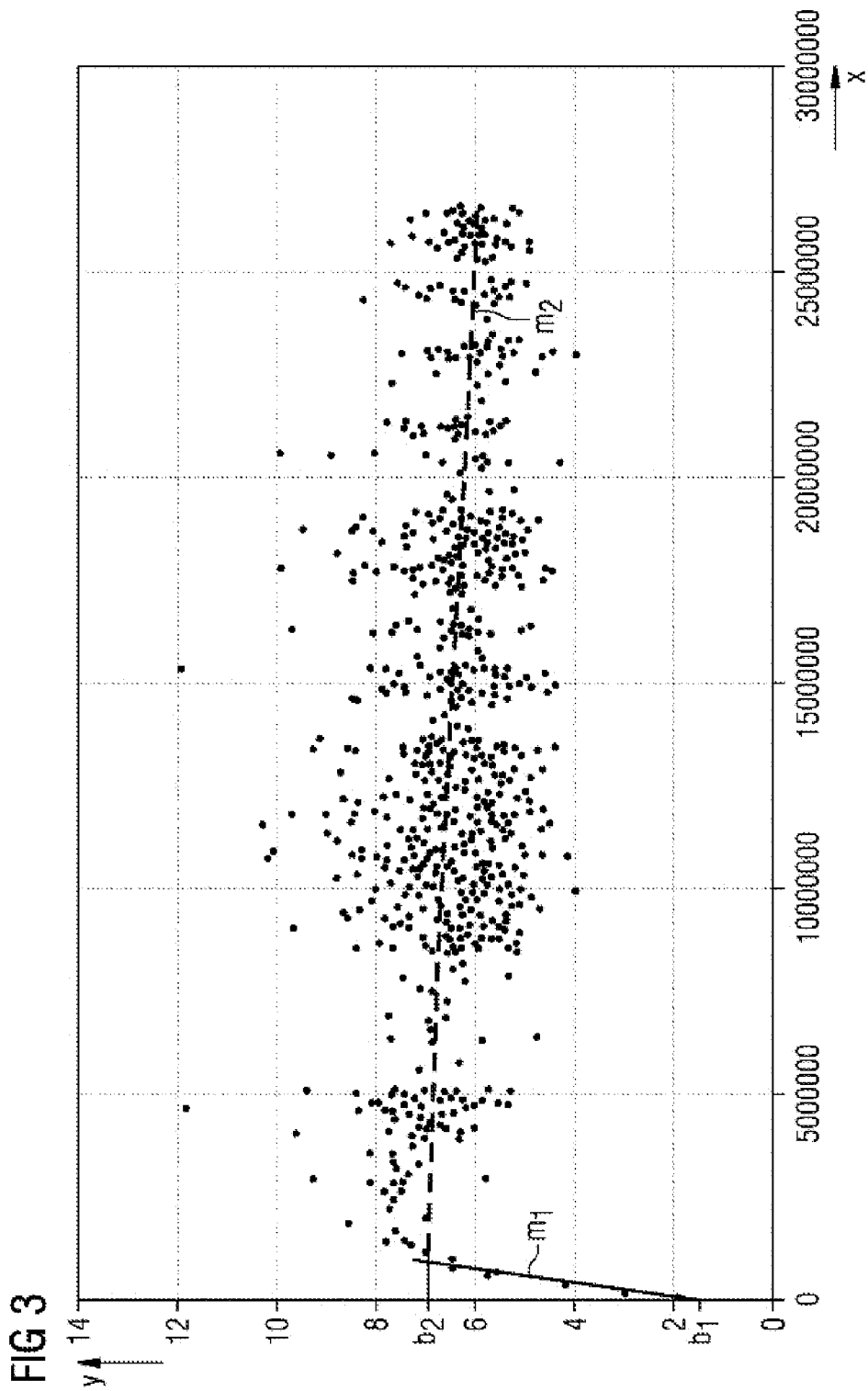

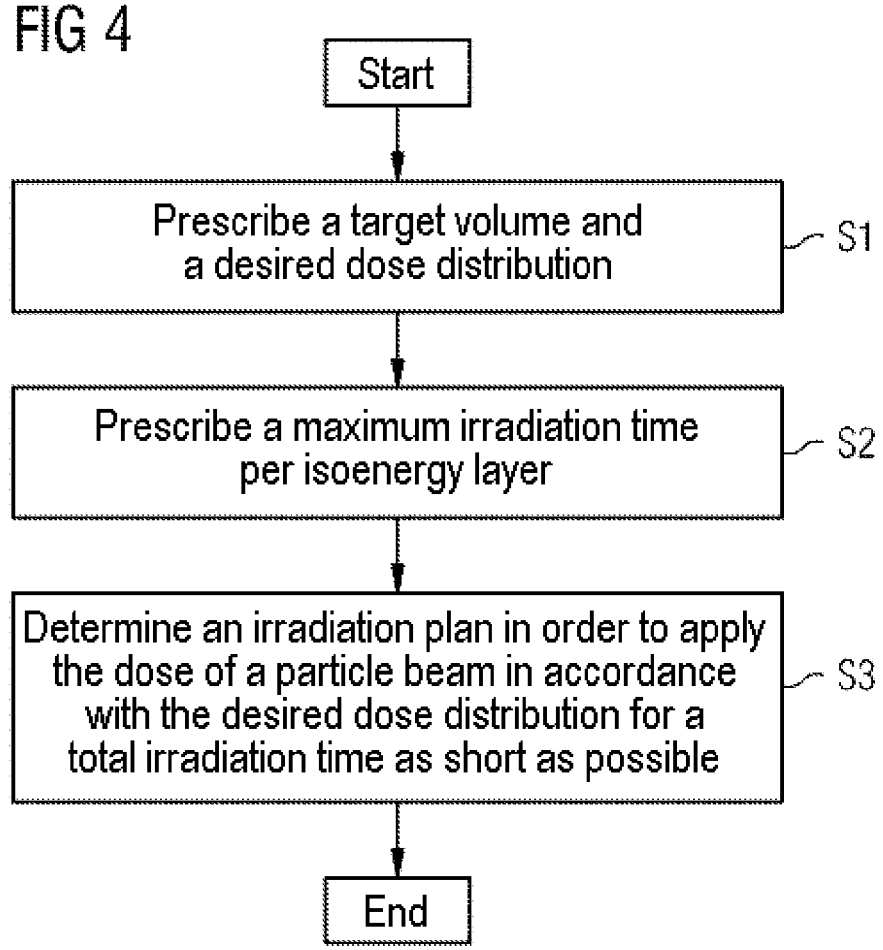

METHOD AND DEVICE FOR DETERMINING AN IRRADIATION PLAN FOR A PARTICLE IRRADIATION SYSTEM

This application is the National Stage of International Application No. PCT/EP2013/056644, filed Mar. 28, 2013, which claims the benefit of DE 10 2012 208 027.9, filed May 14, 2012. The entire contents of these documents are hereby incorporated herein by reference.

BACKGROUND

The present embodiments relate to determining an irradiation plan for a particle irradiation system.

By way of example, an irradiation plan that defines control parameters for irradiating a test object is drawn up in advance during therapy planning in the case of particle therapy. The irradiation plan is used to plan the irradiation of an object in accordance with specific stipulations (e.g., target volume and dose distribution).

Particle therapy is an established method used, for example, to irradiate tissue attacked by tumorous diseases. In particle therapy, charged particles such as, for example, protons, carbon ions, or other ions are accelerated to high energies, shaped into a particle beam and guided via a high-energy beam transport system to one or more irradiation chambers. The target volume of the treatment object is irradiated with the aid of the particle beam in an irradiation chamber. Tissue outside the target volume may also be irradiated if so required.

In particle therapy with an active scanning method, individual grid points are irradiated with the aid of particle beams of different intensity (e.g., number of particle values per time unit). The different intensities are able to encompass a plurality of orders of magnitude. In this case, a monitoring system of the particle irradiation system is used for location measurement and intensity measurement using ionization chambers.

In this case, a grid point is not to be understood as a mathematic point in the target volume. Instead of this, the grid point defines a small surface or layer, mostly in the target volume, which is orthogonal to the particle beam. The particle beam thereby traverses the grid point or the layer defined by the grid point, and deposits along a track the dose to be applied. The largest proportion of the dose is applied or is intended to be applied in the "Bragg peak".

SUMMARY AND DESCRIPTION

The scope of the present invention is defined solely by the appended claims and is not affected to any degree by the statements within this summary.

The present embodiments may obviate one or more of the drawbacks or limitations in the related art. For example, patient penetration in particle therapy with active energy variation is shortened.

Within the scope of one or more of the present embodiments, a method for determining (e.g., in an automatic fashion) an irradiation plan for a particle irradiation system is provided. The particle irradiation system is used to irradiate a target volume within a test object in accordance with the irradiation plan with the aid of a particle beam. Proceeding from a prescribed target volume and a predetermined dose distribution (e.g., desired dose distribution), in this case, the irradiation plan is determined within the target volume in order to deposit or to apply the dose of the particle beam with a high quality (e.g., as exactly as possible in accordance with the predetermined dose distribution within the target volume) with the aid of the irradiation plan. According to one or more of the present embodiments, when determining the irradiation plan, an irradiation time is taken account of so that the irradiation plan is determined such that the irradiation time is as short as possible.

For example, when drawing up the irradiation plan, the time during which a patient is irradiated in the course of the particle therapy may be shortened by taking account of the irradiation time, and this has a positive influence on the patient penetration.

For example, the irradiation plan may be determined with the aid of an optimization method in which a measure is calculated as a function of the quality of the dose distribution in accordance with the irradiation plan and of the irradiation time. The optimization method determines the irradiation plan for which the measure has a best value. The measure is better, the better the quality of the dose distribution in accordance with the irradiation plan and the shorter the irradiation time.

The quality of the dose distribution and the shortness of the irradiation time are in general two conflicting requirements based on the irradiation plan. The cost function or optimization function with the aid of which the optimization method determines the measure includes, for example, at least one term for evaluating the quality of the dose distribution, and at least one term for evaluating the irradiation time. The term or the terms for evaluating the quality of the dose distribution result in a better measure the more the dose distribution in accordance with the irradiation plan corresponds to the prescribed desired dose distribution. The quality of the dose distribution (e.g., the quality with which the dose of the particle beam is applied with the aid of the irradiation plan) may be determined in this case (e.g., with reference to the observance of specific tolerance limits of organs at risk) with the aid of dose/volume histograms, the observance of tolerance limits with regard to the dose distribution within the target volume (e.g., "dose constraints of planning target volume") and/or the correspondence between actual dose distribution and desired dose distribution (e.g., the absolute values of the actual dose distribution are to correspond, in accordance with the irradiation plan, to the absolute values of the desired dose distribution). The quality definition is valid for the present embodiments.

According to one or more of the present embodiments, the irradiation time may be a total irradiation time (e.g., total temporal duration of the irradiation of the test object with the aid of the particle beam) or an irradiation time of a specific isoenergy layer of the target volume.

When a spill (e.g., accelerator cycle) is to be provided in addition to the irradiation of the same isoenergy layer, the irradiation time of the isoenergy layer increases sharply, since the generation of a new spill lasts approximately 4 to 5 s. As optimization criterion, the effect of the irradiation time of the isoenergy layer is that in addition to the optimization of the sum of all the numbers of particles for the isoenergy layer in cooperation with the intensity level set for the isoenergy layer, the grid points of the isoenergy layer are irradiated as far as possible with a low number of spills (e.g., with only one spill).

In this case, the total irradiation time T is determined by the following equation (1), where numSp corresponds to the number of spills, where TBschl corresponds to that time interval (approximately 4-5 s) that the particles of a new spill require in order to be accelerated up to the required speed, and where $TSp_i$ corresponds to the time during which the ith spill in the target volume is irradiated.

$$T = numSp \times TBschl + \sum_{i=1}^{numSp} TSp_i. \quad (1)$$

The time $TSp_i$ is calculated with the aid of equation (2), where $numPartSp_i$ corresponds to the number of the particles in the ith spill, where $nomInt_i$ corresponds to the nominal intensity of the ith spill, and where EffF corresponds to the efficiency factor of the particle irradiation system.

$$TSp_i = \frac{numPartSp_i}{nomInt_i \times EffF}. \quad (2)$$

From equation (1), the number (numSp) of the spills strongly influences the total irradiation time. Consequently, when used with equation (1), the method according to one or more of the present embodiments will attempt, firstly, to use as far as possible only one spill per isoenergy layer and, secondly, to keep the number of the irradiated isoenergy layers as small as possible.

A further variant for calculating the irradiation time $TSp_i$ of the ith spill is specified in the following equation (3).

$$TSp_i = \sum_{j=1}^{numSpot_i} \frac{numPartSpot_{j,i}}{Int_{j,i}} \quad (3)$$

The term $numSpot_i$ corresponds to the number of the grid points that are irradiated by the ith spill, and $numPartSpot_{j,i}$ corresponds to the number of the particles that are applied from the ith spill at the jth grid point of the ith spill. $Int_{j,i}$ specifies the intensity with which the jth grid point is irradiated by the ith spill. The intensity $Int_{j,i}$ is, in turn, calculated by the following equation (4).

$$Int_{j,i} = m \times \sum_{k=1}^{j} numPartSpot_{k,i} + b \quad (4)$$

The term m corresponds to a slope of a straight line, and b corresponds to a y-axis intercept of the straight line. The straight line describes an empirically determined relationship between the intensity of a spill as a function of the number of particles.

As will later be explained in more detail with FIG. 3, the calculation of the irradiation time of a spill with the aid of equations (3) and (4) takes account of the fact that the intensity during a spill is not constant, but may fall, for example, linearly with the number of particles. In this case, the number of particles corresponds to the number of particles that, starting from the beginning, have been output by the ith spill up to and including the irradiation of the jth grid point with reference to whose irradiation intensity is determined. In other words, this number of particles corresponds to the sum $$\sum_{k=1}^{j} numPartSpot_{k,j}.$$

The more exactly the irradiation time of a spill is calculated, the more accurately effects on the irradiation time of a spill, and thus on the total irradiation time may be estimated. In comparison to the prior art, it is thereby advantageously possible to optimize the irradiation plan more effectively (e.g., with reference to the total irradiation time).

In accordance with one embodiment, when determining the intensity, two different straight lines are distinguished as a function of the number of particles (e.g., a first, rising branch and a second, falling branch). In other words, both the slope m and the y-axis intercept have a different value as a function of whether the number of particles is less than or greater than an empirically determined threshold of the number of particles (see reference symbol 31 in FIG. 3).

The slope m and the y-axis intercept both of the rising branch and of the falling branch may be determined by using any desired optimization method (e.g., method of least squares) in order to determine the parameters (e.g., slope, y-axis intercept) starting from measurement points acquired by way of example (e.g., intensity against number of particles). It is to be taken into account, for example, in this case that the y-axis intercept of the falling branch is a function of the efficiency factor of the particle irradiation system.

According to one or more of the present embodiments, the irradiation plan may be determined as a function of the efficiency factor of the particle irradiation system. In this case, the efficiency factor corresponds to the average ratio of the actual or measured intensity to, for example, the intensity prescribed in accordance with the irradiation plan.

Given that the efficiency factor is taken into account when drawing up the irradiation plan, it is, for example, advantageously possible to specify a width of variation of the irradiation time per isoenergy layer, or of the total irradiation time.

The efficiency factor may be determined in this case for each spill with the aid of the following equation (5):

$$EffF_i = \frac{realInt_i}{nomInt_i} \quad (5)$$

The term $EffF_i$ corresponds to the efficiency factor of the ith spill. $nomInt_i$ corresponds to the nominal intensity of the accelerator of the particle irradiation system for the ith spill, and $realInt_i$ corresponds to the real intensity of the accelerator given the selected nominal intensity $nomInt_i$ for the ith spill.

The efficiency factor EffF may also be determined globally in accordance with the following equation (6):

$$EffF = \frac{1}{numSp} \sum_{i=1}^{numSp} \frac{realInt_i}{nomInt_i} \quad (6)$$

As in the case of equation (5), $nomInt_i$ corresponds to the nominal intensity of the accelerator for the ith spill, and $realInt_i$ corresponds to the real intensity of the accelerator given the selected nominal intensity $nomInt_i$ for the ith spill. numSp specifies the number of spills.

The efficiency factor EffF may be calculated with the aid of one of the following equations (7) and (8).

$$EffF = \sum_{i=1}^{numSp} \frac{numPartSp_i}{nomInt_i} \times \frac{1}{TSp_i} \times \frac{numPartPlan}{numPartSp_i} \quad (7)$$

The term numSp corresponds to the number of spills, and $nomInt_i$ corresponds to the nominal intensity of the ith spill. $numPartSp_i$ corresponds to the number of particles of the ith spill, $TSP_i$ corresponds to the irradiation time of the ith spill, and numPartPlan corresponds to the total number of particles in accordance with the irradiation plan.

The term $numPartSp_i$ in equation (7) may be shortened, the result being equation (8):

$$EffF = \sum_{i=1}^{numSp} \frac{numPartPlan}{nomInt_i \times TSp_i} \quad (8)$$

According to one or more of the present embodiments, the efficiency factor may also be set as optimization parameter when the result is to shorten the total irradiation time by more than a prescribed timing threshold.

By way of example, the efficiency factor may be increased by up to 20% by increasing the source current of the ion source of the particle irradiation system. According to one or more of the present embodiments, the slight increase in efficiency may be set only when it is thereby possible to attain a superproportional reduction in the irradiation time.

According to one or more of the present embodiments, it is also possible to prescribe a maximum irradiation time or a maximum number of spills for an isoenergy layer.

In one embodiment, each isoenergy layer may be prescribed an individual or the same maximum irradiation time or a maximum number of spills (e.g., exactly one spill per isoenergy layer). When each isoenergy layer is irradiated with the aid of only one spill, this may lead to a better dose distribution (e.g., for the irradiation of moving objects), since the grid points of the same isoenergy layer may be provided with the appropriate energy or dose within a comparatively short time interval.

In one embodiment, a maximum total irradiation time may be prescribed.

The stipulation of the maximum total irradiation time may, firstly, be modified such that the irradiation plan determined according to one or more of the present embodiments reliably has a total irradiation time that is not longer than the prescribed maximum total irradiation time. In one embodiment, the cost function to be optimized may, however, not consider the total irradiation time to be negative (e.g., apply an appropriate surcharge (penalty)) until the total irradiation time is longer than the maximum total irradiation time. In this case, the penalty may have a nonlinear magnitude, which provides that the penalty is slight given a small overshooting of the maximum total irradiation time but, given a larger overshooting, increases nonlinearly with the difference from the maximum total irradiation time.

Taking a negative account of the overshooting of a prescribed limit (e.g., the maximum irradiation time of an isoenergy layer or of a maximum number of spills for an isoenergy layer) in the form of a nonlinearly increasing penalty that is then taken into account in the case of the cost function to be optimized may also be used for other embodiments.

A device for determining an irradiation plan for a particle irradiation system is also provided. The particle irradiation system in this case irradiates a target volume within a test object with the aid of a particle beam as a function of the specific irradiation plan. The device includes an input device, a computing device and an output device. The target volume and a predetermined dose distribution (e.g., desired dose distribution) are prescribed for the device by the input means. The computing device determine the irradiation plan such that the particles of the particle beam are output in accordance with the predetermined dose distribution in the target volume. The irradiation plan is output with the aid of the output device. According to one or more of the present embodiments, the computing device takes account of an irradiation time when determining the irradiation plan. The computing device determines the irradiation plan such that the irradiation time is as short as possible (e.g., minimized).

A particle irradiation system having a device according to one or more of the present embodiments is also provided.

The advantages of the device according to one or more of the present embodiments and of the particle irradiation system according to one or more of the present embodiments correspond substantially to the advantages of the method according to one or more of the present embodiments. Given that this has been set forth in detail above, there is no need here for any repetition.

A computer program product (e.g., a software product) that may be loaded into a memory of a programmable controller or into a computing device of a particle irradiation system is provided. The computer program product may be used to execute all, or various ones, of previously described embodiments of the method when the computer program product is running in the controller. In this case, the computer program product may use program coding or instructions (e.g., libraries and auxiliary functions) in order to implement the appropriate embodiments of the method. In other words, the aim of the claim directed to the computer program product is, for example, to protect a software product with the aid of which one of the above-described embodiments of the method may be executed, or which executes the embodiment. Software may be a source code (e.g., C++) that has still to be compiled and linked or needs only to be interpreted. Software may also be an executable software code that, in order to be executed, may further only be loaded into the appropriate computing device or the controller.

An electronically readable data carrier (e.g., a non-transitory data carrier such as a DVD, a magnetic tape or a USB stick on which electronically readable control information such software described above is stored) is provided. All embodiments of the method previously described may be carried out when the control information (e.g., software) is read from the data carrier and stored in the controller or an arithmetic logic unit of a particle irradiation system.

One or more of the present embodiments are, for example, suitable for increasing the patient penetration in particle therapy. The present invention is not limited to the exemplary field of application, since the present invention may be used wherever energy and/or a dose is applied in a target volume with the aid of particles.

BRIEF DESCRIPTION OF THE DRAWINGS

FIG. 2 is a schematic of an example of how a target volume is irradiated by a particle irradiation system;

FIG. 3 illustrates an example of an intensity profile against the number of particles for a spill; and FIG. 4 illustrates a program flowchart of one embodiment of a method.

DETAILED DESCRIPTION

Figure 1:
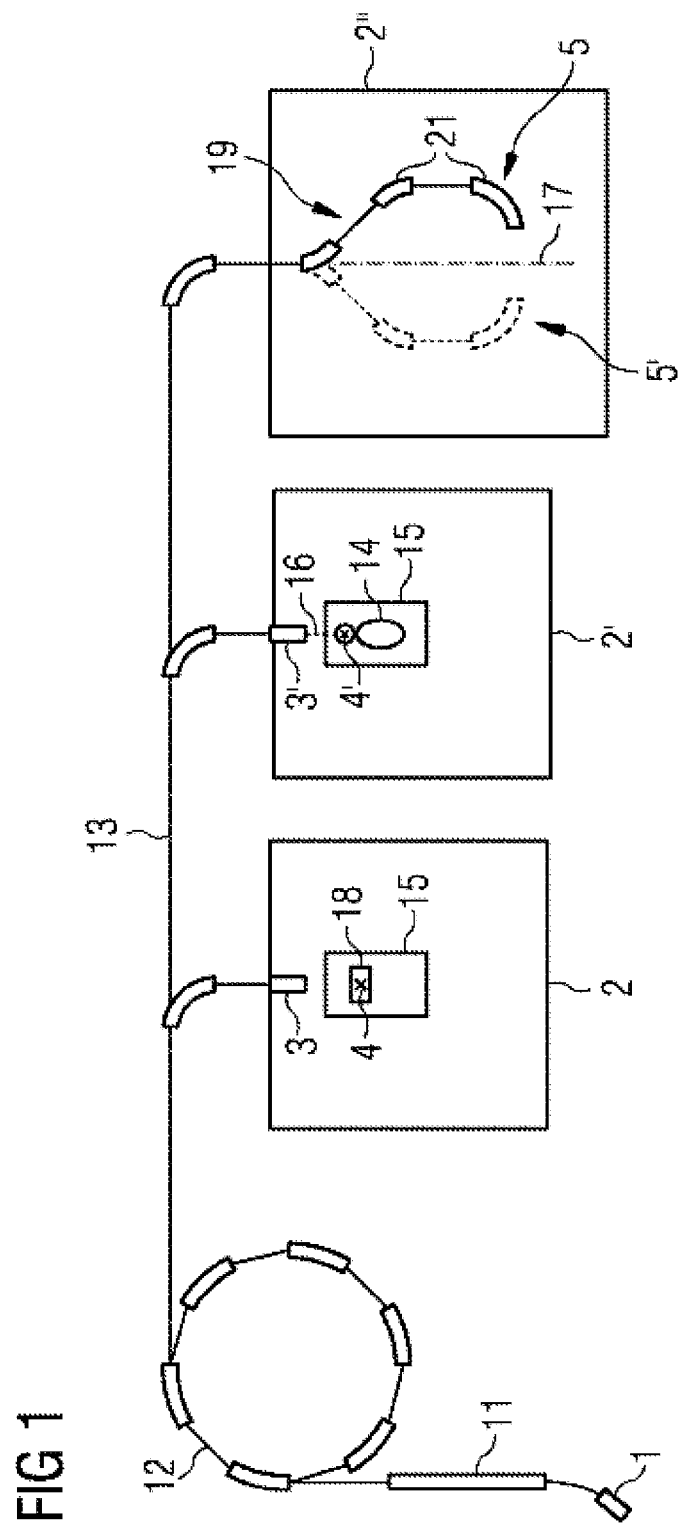
FIG. 1 is a schematic overview of the structure of one embodiment of a particle irradiation system.

One embodiment of a particle irradiation system 20 is illustrated schematically in FIG. 1. The particle irradiation system 20 irradiates a patient 14 lying on a positioning device 15 (e.g., a table; see irradiation chamber 2') with a beam including particles 16. The beam is denoted below as particle beam 16. By way of example, such a particle beam 16 may be used to irradiate a tumor of the patient 14 with the aid of high-energy particles. However, as illustrated in the irradiation chamber 2 by the example of a water phantom 18, the particle irradiation system 20 may also be used to irradiate a nonliving object 18.

Protons, pions, helium ions, carbon ions, but also ions of other elements, are examples of particles used. For this purpose, the appropriate particles are produced in a particle source or ion source 1 and accelerated to a first energy level in a pre-accelerator 11 (e.g., a linear accelerator). Subsequently, the particles are accelerated to an energy used for irradiation in a circular accelerator 12 (e.g., a synchrotron or cyclotron). The particle beam emerging from the circular accelerator 12 is transported by a high-energy beam transport system 13 into one or more irradiation chambers 2, 2', 2", and used at the one or more irradiation chambers 2, 2', 2" to irradiate a target volume of a patient 14. The irradiation is performed from a fixed direction so that the body 14, 18 to be irradiated is arranged fixed in space by the positioning device 15 in the irradiation chamber 2, 2'. The irradiation chambers 2, 2' are therefore also denoted as fixed-beam chambers. By contrast, there is present in the irradiation chamber 2" a gantry 19 that is arranged to move about an axis 17 (e.g., to rotate) and by which the body to be irradiated may be irradiated from various directions. For this purpose, the particle beam 16 is directed as appropriate with the aid of a beam guide 21 of the gantry 19 onto the body to be irradiated. Two positions 5, 5' are illustrated in FIG. 1, although a plurality of positions may be used.

In the irradiation chambers 2, 2', the particle beam 16 emerges from a beam outlet 3, 3' and impinges on the body 14 or 18 in which the target volume to be irradiated is located. The target volume may be in the isocenter 4, 4' of the respective irradiation chamber 2, 2'.

FIG. 2 is a schematic of a target volume 6 that is irradiated by a particle beam 16 produced by a particle irradiation system 20. In addition to an irradiation planning device 10, the particle irradiation system 20 includes a beam producing device 30, a raster scanning device 23 and a controller 22 for the raster scanning device 23. The raster scanning device 23 includes a first particle deflector 24 and a second particle deflector 25 that respectively include magnets, for example. The two particle deflectors 24, 25 may be used to deflect the particle beam 16 both horizontally and vertically, and this is illustrated by the mutually perpendicular arrows x, y. Consequently, the raster scanning device 23 is capable of directing the particle beam 16 onto any desired point $(x_i, y_i)$ of an area within the x-y plane. Together with the particle energy respectively used, each of the points is denoted as scanning spot, grid point or sampling point. Accordingly, a grid point is determined, firstly, by the alignment of the particle beam 16 (e.g., x- or y-direction) and, secondly, by a corresponding particle energy. In other words, a plurality of grid points having different particle energies exist for specific x- and y-coordinates. In this case, the particle energy determines the coordinate in the z-direction (e.g., perpendicular to the x- or y-axis), while the z-position may lie further in the direction of the particle beam 16 within the target volume 6, the higher the particle energy. Since, however, the penetration depth is a function of the tissue or material that the particle beam 16 traverses, the above relationship holds true exactly only for the same x- and y-positions.

The target volume 6 to be irradiated by the particle beam 16 is irradiated in this case in the form of isoenergy layers 7-9. Particles having the same energy are respectively applied in this case at the grid points of the same isoenergy layer 7-9. Assuming that on the way to the appropriate isoenergy layer 7-9, the particle beam 16 traverses a homogeneous volume, the isoenergy layers 7-9 lie at right angles to the z-axis, as is presented in FIG. 2 for the sake of simplification.

In order to set the particle beam 16 to an appropriate isoenergy layer 7-9, the particles of the particle beam 16 are respectively allotted an appropriate initial energy by accelerating the particles to a speed corresponding to the initial energy. The initial energy describes the energy of a particle that the particle has before impinging on the object 14 or 18. In order to irradiate that isoenergy layer 7 that is situated nearest the beam outlet 3, 3' (e.g., furthest left in FIG. 2), use is made of particles having the lowest energy, whereas in order to irradiate that isoenergy layer 9 that is arranged at the greatest distance from the beam outlet 3, 3' (e.g., furthest right in FIG. 2), use is made of the particles having the highest energy.

In order to irradiate the total target volume 6, the isoenergy layers 7-9 are irradiated sequentially in a fashion generally starting with the isoenergy layer 9 that is furthest removed from the beam outlet 3, 3', and then continuing with the respectively adjacent isoenergy layer. In order to irradiate specific grid points with the same isoenergy layer 7-9 with different energies, the time interval during which the appropriate grid point is irradiated by the particle beam 16 is, for example, varied. The longer the appropriate grid point is irradiated by the particle beam 16, the more energy (e.g., higher dose) is deposited at the appropriate grid point.

In the case of the target volume 6 illustrated in FIG. 2, the isoenergy layer 8 is currently being irradiated by the particle beam 16, while the three isoenergy layers 9 have already been irradiated, and four isoenergy layers 7 situated further left (in FIG. 2) are still waiting to be irradiated.

Before the target volume 6 is irradiated, an irradiation plan, by which the scanning or sampling of the target volume 6 is performed with the aid of the particle beam 16, is drawn up. For example, in this case, the irradiation plan determines control parameters for controlling the particle irradiation system 20. The drawing up of the irradiation plan is carried out in this case with the aid of an irradiation planning device 10 (e.g., a PC).

In order to carry out the actual irradiation, the irradiation plan is passed on by the irradiation planning device 10 to the beam producing device 30 and the controller 22 of the raster scanning device 23. The irradiation planning device 10 is illustrated in FIG. 2 as if being a component of the particle irradiation system 20. In one embodiment, the irradiation plan drawn up by the irradiation planning device 10 may be loaded onto a data carrier 29 via which the irradiation plan is then loaded into the particle irradiation system 20. In this case, the irradiation planning device 10 and the particle irradiation system 20 may not be interconnected using communication technology. A certain period of time (e.g., several days) may lie between the drawing up of the irradiation plan and the irradiation carried out with the aid of the irradiation plan.

In order to draw up the irradiation plan, the irradiation planning device 10 uses the position and the dimensions of the target volume 6 to be irradiated (e.g., a tumor to be irradiated). When irradiating a patient 14, the nature of the tissue that is being transirradiated by the particle beam 16 on the way to the target volume 6 is to be known. The information may be determined, for example, by a computer or magnetic resonance tomography, and then transmitted to the irradiation planning device 10 via an appropriate input device 26. With the aid of a computing device 27 (e.g., a processor) of the irradiation planning device 10, the irradiation planning device 10 determines the irradiation plan proceeding from the information and a predetermined dose distribution (e.g., desired dose distribution). In this case, the irradiation plan specifies, for example, how many particles of a specific energy are to be applied at a grid point.

During the irradiation, a patient is to be fixed in order to exclude movement of the target volume 6 as far as possible. The irradiation time is to be kept as short as possible for this reason. A short irradiation time advantageously enables a higher patient penetration. The dose distribution in accordance with the irradiation plan is to correspond as well as possible to the desired dose distribution. Given that in accordance with one or more of the present embodiments the irradiation time of an isoenergy layer or the total irradiation time is already minimized in drawing up and optimizing the irradiation plan, an irradiation plan drawn up according to one or more of the present embodiments may advantageously lead to a short irradiation time and to a good quality of the dose distribution. Depending on weighting in accordance with evaluation criteria (e.g., optimization penalties), more value may be placed on the quality of the dose distribution or on the irradiation time.

The intensities for all grid points irradiated by a spill are plotted in FIG. 3 against the number of particles. At the start of the spill, the number of particles has the value 0 and subsequently corresponds to the sum of the particles that have already been shot from the spill into the target volume with reference to the current grid point and additionally with reference to the grid points irradiated earlier in time. In other words, the number of particles rises steadily from grid point to grid point. The intensity firstly rises sharply up to a specific number of particles 31 and subsequently falls slightly. For example, the method of least squares may be used to determine a slope m1 (e.g., a positive slope) and a y-axis intercept b1 for the rising branch, and to determine a slope m2 (e.g., a negative slope) and a y-axis intercept b2 for the falling branch. A corresponding straight line segment is illustrated in FIG. 3 both for the rising and for the falling branch.

Given that, in determining an irradiation plan, the intensity to be generated by a spill is calculated with the aid of the straight line segments illustrated in FIG. 3, the intensity taken into account in determining the irradiation plan agrees better with the intensity later applied than is the case in the prior art. It is thereby advantageously possible to determine more accurately both the irradiation time of a spill or an isoenergy layer and also the total irradiation time in accordance with the irradiation plan. This leads to the ability to more accurately calculate the effects on the irradiation time of measures according to one or more of the present embodiments for the purpose of reducing the irradiation time, so that it is possible at least with a greater certainty (e.g., with a lesser deviation from the actual result) to draw up an irradiation plan optimized with respect to the irradiation time.

A method according to one or more of the present embodiments is illustrated in FIG. 4 in the form of a flowchart plan.

In act S1, the target volume and a desired dose distribution or target dose distribution is prescribed or defined. In a following act step S2, a maximum irradiation time that, for example, prescribes how long the respective isoenergy layer may be irradiated to the maximum with the aid of a particle beam is prescribed or defined per isoenergy layer.

In act S3, the irradiation plan is determined in order to apply the energy of the particle beam in accordance with the desired dose distribution with the aid of a total irradiation time that is as short as possible. The maximum irradiation time prescribed per isoenergy layer is not overshot.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining and using an irradiation plan for a particle irradiation system, the method comprising:
   defining a target volume within a test object and a predetermined dose distribution;
   determining the irradiation plan in order to apply an energy of a particle beam in accordance with the predetermined dose distribution in the target volume, wherein the irradiation plan specifies a number of particles of a specific energy to be applied at a point in the target volume within the test object; and
   irradiating, with the particle irradiation system, the target volume within the test object with the particle beam as a function of the irradiation plan,
   wherein the irradiation plan is determined as a function of a defined maximum irradiation time at an isoenergy layer in the target volume and as a function of an efficiency factor of the particle irradiation system, the efficiency factor being based on a ratio of a measured intensity of the particle irradiation system to an intensity of the particle irradiation system prescribed in the irradiation plan, and
   wherein determining the irradiation plan comprises determining the irradiation plan such that the irradiation time is minimized.

2. The method of claim 1, wherein the irradiation plan is determined with the aid of an optimization method, the optimization method determining a measure as a function of a difference between the predetermined dose distribution and an actual dose distribution, and of the irradiation time,
   wherein the optimization method determines the irradiation plan with the aid of a best measure, and wherein when the measure is better, the better the predetermined dose distribution corresponds to the actual dose distribution and the shorter the irradiation time.

3. The method of claim 1, wherein the irradiation time further corresponds to a total irradiation time of the irradiation plan.

4. The method of claim 3, wherein the total irradiation time T is determined as follows $$T = numSp \times TBschl + \sum_{i=1}^{numSp} TSp_i,$$

wherein numSp corresponds to a number of spills,
wherein TBschl corresponds to a time interval in which particles of a new spill are accelerated,
wherein $TSp_i$ corresponds to the irradiation time of the ith spill,
wherein the irradiation time $TSp_i$ of the ith spill is determined as follows $$TSp_i = \frac{numPartSp_i}{nomInt_i \times EffF}$$

wherein $numPartSp_i$ corresponds to the number of the particles in the ith spill,
wherein $nomInt_i$ corresponds to the nominal intensity of the ith spill, and
wherein EffF corresponds to the efficiency factor of the particle irradiation system.

5. The method of claim 4, wherein the irradiation time $TSp_i$ of the ith spill is determined as follows $$TSp_i = \sum_{j=1}^{numSpot_i} \frac{numPartSpot_{j,i}}{Int_{j,i}},$$

wherein $numSpot_i$ corresponds to the number of the spots of the ith spill,
wherein $numPartSpot_{j,i}$ corresponds to the number of the particles of the jth spot in the ith spill,
wherein $Int_{j,i}$ corresponds to the intensity during the irradiation of the jth spot in the ith spill,
wherein the intensity $Int_{j,i}$ is determined as follows $$Int_{j,i} = m \times \sum_{k=1}^{j} numPartSpot_{k,i} + b,$$

wherein m corresponds to a slope of a straight line, and b corresponds to a y-axis intercept of the straight line, and
wherein the straight line describes an empirically determined profile of the intensity of a spill against the particle number.

6. The method of claim 5, wherein the slope has a first slope value, and the y-axis intercept has a first intercept value when the number of particles is less than a threshold value for the number of particles,
wherein the slope has a second slope value, and the y-axis intercept has a second intercept value when the number of particles is greater than the threshold value for the number of particles, wherein the first slope value is positive, and the second slope value is negative, and
wherein the second intercept value is a linear function of the efficiency factor.

7. The method of claim 1, wherein the efficiency factor $EffF_i$ for the ith spill is determined as follows $$EffF_i = \frac{realInt_i}{nomInt_i},$$

wherein $realInt_i$ corresponds to the real intensity of the particle irradiation system for the ith spill, and
wherein $nomInt_i$ corresponds to the nominal intensity of the particle irradiation system for the ith spill.

8. The method of claim 1, wherein the efficiency factor EffF is determined as follows $$EffF = \frac{1}{numSp} \sum_{i=1}^{numSp} \frac{realInt_i}{nomInt_i},$$

wherein numSp corresponds to the number of spills,
wherein $realInt_i$ corresponds to a real intensity of the particle irradiation system, and
wherein $nomInt_i$ corresponds to the nominal intensity of the particle irradiation system.

9. The method of claim 1, wherein the efficiency factor EffF is determined as follows $$EffF = \sum_{i=1}^{numSp} \frac{numPartPlan}{nomInt_i \times TSp_i},$$

wherein numSp corresponds to the number of spills,
wherein $nomInt_i$ corresponds to a nominal intensity of the ith spill,
wherein $TSp_i$ corresponds to the irradiation time of the ith spill, and
wherein numPartPlan corresponds to the total number of the particles in accordance with the irradiation plan.

10. The method of claim 1, wherein the efficiency factor is improved when a total irradiation time is shortened by more than a prescribed timing threshold.

11. The method of claim 1, further comprising:
defining a maximum number of spills for the isoenergy layer.

12. The method of claim 1, further comprising a maximum total irradiation time.

13. A device for determining and using an irradiation plan, the device comprising:
an input device;
a computer in communication with the input device;
an output device in communication with the computer; and
a particle irradiation system,
wherein the particle irradiation system is operable to irradiate a target volume within a test object with a particle beam as a function of the irradiation plan,
wherein the input device is operable to define the target volume and a predetermined dose distribution, and
wherein the computer is configured to determine the irradiation plan in order to apply energy of the particle beam in accordance with the predetermined dose distribution in the target volume, wherein the irradiation plan specifies a number of particles of a specific energy to be applied at a point in the target volume within the test object, wherein the output device is configured to output the irradiation plan to the particle irradiation system, and wherein the computer is configured to determine the irradiation plan as a function of a defined maximum irradiation time at an isoenergy layer in the target volume and as a function of an efficiency factor of the particle irradiation system, the efficiency factor being based on a ratio of a measured intensity of the particle irradiation system to an intensity of the particle irradiation system prescribed in the irradiation plan, and wherein the irradiation plan is determined such that the irradiation time is minimized.

14. A system comprising a device for determining and using an irradiation plan, the device comprising:

an input device;

a computer in communication with the input device;

an output device in communication with the computer; and a particle irradiation system, wherein the particle irradiation system is operable to irradiate a target volume within a test object with a particle beam as a function of the irradiation plan, wherein the input device is operable to define the target volume and a predetermined dose distribution, and wherein the computer is configured to determine the irradiation plan in order to apply energy of the particle beam in accordance with the predetermined dose distribution in the target volume, wherein the irradiation plan specifies a number of particles of a specific energy to be applied at a point in the target volume within the test object, wherein the output device is configured to output the irradiation plan, and wherein the computer is configured determine the irradiation plan as a function of a defined maximum irradiation time at an isoenergy layer in the target volume and as a function of an efficiency factor of the particle irradiation system, the efficiency factor being based on a ratio of a measured intensity of the particle irradiation system to an intensity of the particle irradiation system prescribed in the irradiation plan, and wherein the irradiation plan is determined such that the irradiation time is minimized.

15. A non-transitory computer program product comprising a non-transitory computer-readable storage medium having a program executable by a programmable controller of a particle irradiation system to determine and use an irradiation plan for the particle irradiation system, the program comprising instructions, the instructions comprising:

defining a target volume within a test object and a predetermined dose distribution;

determining the irradiation plan in order to apply an energy of a particle beam in accordance with the predetermined dose distribution in the target volume, wherein the irradiation plan specifies a number of particles of a specific energy to be applied at a point in the target volume within the test object; and irradiating, with the particle irradiation system, the target volume within the test object with the particle beam as a function of the irradiation plan, wherein the irradiation plan is determined as a function of a defined maximum irradiation time at an isoenergy layer in the target volume and as a function of an efficiency factor of the particle irradiation system, the efficiency factor being based on a ratio of a measured intensity of the particle irradiation system to an intensity of the particle irradiation system prescribed in the irradiation plan, and wherein determining the irradiation plan comprises determining the irradiation plan such that the irradiation time is minimized.

16. A non-transitory electronically readable data carrier on which there is stored electronically readable control information configured such that when the non-transitory electronically readable data carrier is used in a controller of a particle irradiation system, the electronically readable control information determines and uses an irradiation plan for the particle irradiation system, the electronically readable control information comprising:

defining a target volume within a test object and a predetermined dose distribution;

determining the irradiation plan in order to apply an energy of a particle beam in accordance with the predetermined dose distribution in the target volume, wherein the irradiation plan specifies a number of particles of a specific energy to be applied at a point in the target volume within the test object; and irradiating, with the particle irradiation system, the target volume within the test object with the particle beam as a function of the irradiation plan, wherein the irradiation plan is determined as a function of a defined maximum irradiation time at an isoenergy layer in the target volume and as a function of an efficiency factor of the particle irradiation system, the efficiency factor being based on a ratio of a measured intensity of the particle irradiation system to an intensity of the particle irradiation system prescribed in the irradiation plan, and wherein determining the irradiation plan comprises determining the irradiation plan such that the irradiation time is minimized.

* * * * *